(12) United States Patent
Carr et al.

(10) Patent No.: US 6,386,021 B1
(45) Date of Patent: May 14, 2002

(54) OXYGEN SENSOR HEATER SERVICE BAY TEST

(75) Inventors: Mark D. Carr, Fenton; Daniel P. Grenn, Highland; Jerry L. Brink, Canton, all of MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 09/505,583

(22) Filed: Feb. 16, 2000

(51) Int. Cl.[7] .............................................. G01M 15/00
(52) U.S. Cl. ...................................................... 73/118.1
(58) Field of Search ............................ 73/23.31, 23.32, 73/116, 117.2, 117.3, 118.1

(56) References Cited

U.S. PATENT DOCUMENTS

| | | | |
|---|---|---|---|
| 4,768,480 A | * | 9/1988 | Grenn et al. |
| 5,392,643 A | | 2/1995 | O'Kennedy et al. ........... 73/118 |
| 5,781,878 A | * | 7/1998 | Mizoguchi et al. ......... 73/118.1 |
| 5,928,303 A | | 7/1999 | Sakai ......................... 701/109 |
| 6,026,639 A | * | 2/2000 | Kumar |

* cited by examiner

Primary Examiner—Eric S. McCall
(74) Attorney, Agent, or Firm—Anthony Luke Simon

(57) ABSTRACT

A diagnostic routine is used for testing an oxygen sensor heater of an internal combustion engine. The oxygen sensor heater is preheated prior to testing. A voltage signal from the oxygen sensor is measured after a predetermined period of time. If the voltage signal is greater than a threshold value after the predetermined period of time has elapsed, the oxygen sensor heater is considered to have failed the diagnostic routine. If the voltage signal is not greater than the threshold value after the predetermined period of time has elapsed, the oxygen sensor is considered to have passed the diagnostic routine.

16 Claims, 3 Drawing Sheets

OXYGEN SENSOR HEATER SERVICE BAY TEST

FIELD OF THE INVENTION

The present invention relates to a diagnostic subroutine for testing an oxygen sensor heater of an internal combustion engine.

BACKGROUND OF THE INVENTION

Internal combustion engines can include an exhaust oxygen sensor, referred to as an $O_2$ sensor, which can be located in the engine exhaust manifold or exhaust piping to monitor the percentage of oxygen contained within the exhaust gases. The oxygen sensor provides a feedback signal in a closed-loop engine control system where an air-fuel mixture ratio is maintained as close to stoichiometric as possible using the signal from the oxygen sensor. Electronic control modules or units are in wide use with two types of oxygen sensors; namely, an unheated type of $O_2$ sensor; and a heated type of $O_2$ sensor. The unheated type of oxygen sensor does not output a voltage signal to the onboard electronic control unit until the sensing unit has reached operating temperature. The heated type oxygen sensor is fully operational within a few seconds of engine startup, regardless of the exhaust gas temperatures. When the sensing element has not yet reached an operating temperature with the heater energized or activated at the initial engine startup, the sensing element is in an inactive state. When the sensing element is in the inactive state, no diagnostic system can make an accurate diagnosis of deterioration of the oxygen sensor.

Oxygen sensors monitor the by-products of combustion in order to regulate the air-fuel mixture. Proper regulation of the air-fuel mixture is necessary to achieve clean burning of the fuel. Strict emission standards are difficult to meet if the fuel is not cleanly burned.

The oxygen sensor generates an output voltage depending on the content of oxygen and the fuel-air mixture at the exhaust. If the exhaust gas is rich in oxygen, the sensor will produce a low voltage, close to zero volts. If the exhaust gas is rich in fuel, the sensor will produce a voltage close to one volt. The output voltage and internal resistance of an oxygen sensor varies with the temperature and the age of the sensor. A cold oxygen sensor has a very high internal resistance, which decreases significantly once the sensor reaches the operating temperature of approximately 300° Celsius. A cold oxygen sensor is unreliable during the engine warm-up phase. During this period, the engine operates in an open loop where data from the oxygen sensor is not used to regulate the air-fuel mixture. The addition of a heater to the oxygen sensor allows the sensor to reach an operating temperature faster than the sensor would if heated only by the engine exhaust gases. The heater allows the internal combustion engine to reach a closed loop mode of operation where the signal from the oxygen sensor is used to regulate the air-fuel mixture more rapidly than relying on engine exhaust gases alone to heat the oxygen sensor. Oxygen sensors become less reliable with age, because physical wear and chemical contamination effect the output voltage and internal resistence of the sensor. Failed oxygen sensors cause an internal combustion engine to run inefficiently, and have an adverse impact on the performance of the vehicle. The amount of air pollutants produced by a vehicle increases directly as a result of an unclean burn. A failed sensor can also increase fuel consumption.

When the heater fails, an oxygen sensor must be heated sufficiently by the engine exhaust until the oxygen sensor reaches the optimal operating temperature. Existing on-board diagnostic routines require that the vehicle be "cold soaked" before the diagnostic routine will be executed. The on-board oxygen sensor heater time-to-activity diagnostic currently requires the vehicle to be cold soaked for approximately eight hours before diagnosing the heater. Vehicle owners may consider it inconvenient when required to leave a vehicle for an extended period of time in order to perform the known oxygen sensor heater diagnostic.

SUMMARY OF THE INVENTION

The oxygen sensor heater service bay test according to the present invention is used to diagnose an oxygen sensor heater in a shorter period of time than required for known diagnostic tests. Currently the existing on-board diagnostic requires an eight hour cold soak before the test is initiated. The present diagnostic routine generally requires that the vehicle be running in park or neutral in the service bay for a calibrateable or predetermined period of time to insure that the oxygen sensors are sufficiently warm. The vehicle is then turned off, and the key is returned to the key-on/engine-off position. The service tool is connected to the internal combustion engine and sends a message to the programable computer module to initiate the heater service bay test. The programable computer module will acknowledge the message and command the test to continue only if the oxygen-sensor-heater-inspection-maintenance-ready flag indicates that the test has never been run before. Once the test has been commanded to run, the service bay test will disable the fuel injectors so that no fuel is delivered when the engine is cranked. The operator is then instructed to crank the vehicle engine to insure that the oxygen sensors will be exposed to a lean environment. The service bay test then measures the sensor voltage. If the voltage is below a calibration or predetermined threshold value, the test will be armed. If the voltage is not below the calibration or predetermined threshold value, the test will be aborted and the operator is instructed to repeat the procedure from the point where the service tool is connected. After the test is armed, the service bay test monitors the sensor voltage. If the sensor voltage reaches a calibratable or predetermined threshold voltage level after a calibratable or predetermined time duration, the sensor would be considered as failing the diagnostic routine. If the sensor voltage does not reach the calibratable voltage level after the calibratable time duration, the sensor is considered as passing the diagnostic routine. At this point, the oxygen-sensor-heater-inspection-maintenance ready flag is set to indicate that a diagnostic test has been performed on this oxygen sensor heater.

The oxygen sensor heater service bay test allows the oxygen sensor heater to be diagnosed within 20 to 30 minutes. The test according to the present invention will improve customer satisfaction by significantly reducing the time required for the customer to have the vehicle at the service center. The test insures that the service center is capable of setting the inspection-maintenance-ready flag for the oxygen sensor heater diagnostic. The test or diagnostic routine, according to the present invention was developed in an effort to reduce the time required to diagnose and service a vehicle with a broken oxygen sensor heater. The test or diagnostic routine according to the present invention can not be used as the on-board diagnostic, since the enabled conditions would not normally be encountered during normal use of the vehicle by the customer.

The present invention allows the oxygen sensor heater to be diagnosed in a timely manner while the vehicle is in for service. The present invention diagnoses the oxygen sensor heater by observing the sensor voltage in a lean environment with the engine off, after the engine has been warmed up. The sensor heater will be considered to have failed the diagnostic routine if the sensor voltage does not remain lean (or low) for a predetermined time.

A diagnostic routine according to the present invention tests an oxygen sensor heater of an internal combustion engine by preheating the oxygen sensor heater, measuring a voltage signal from the oxygen sensor heater after a predetermined period of time, and determining if the voltage signal is greater than a threshold value after the predetermined period of time has elapsed. If the voltage signal is greater than the threshold value, the oxygen sensor heater fails the diagnostic routine. If the voltage signal is not greater than the threshold value, the oxygen sensor heater passes the diagnostic routine.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION OF THE PREFERRED EMBODIMENT

Figure 1:
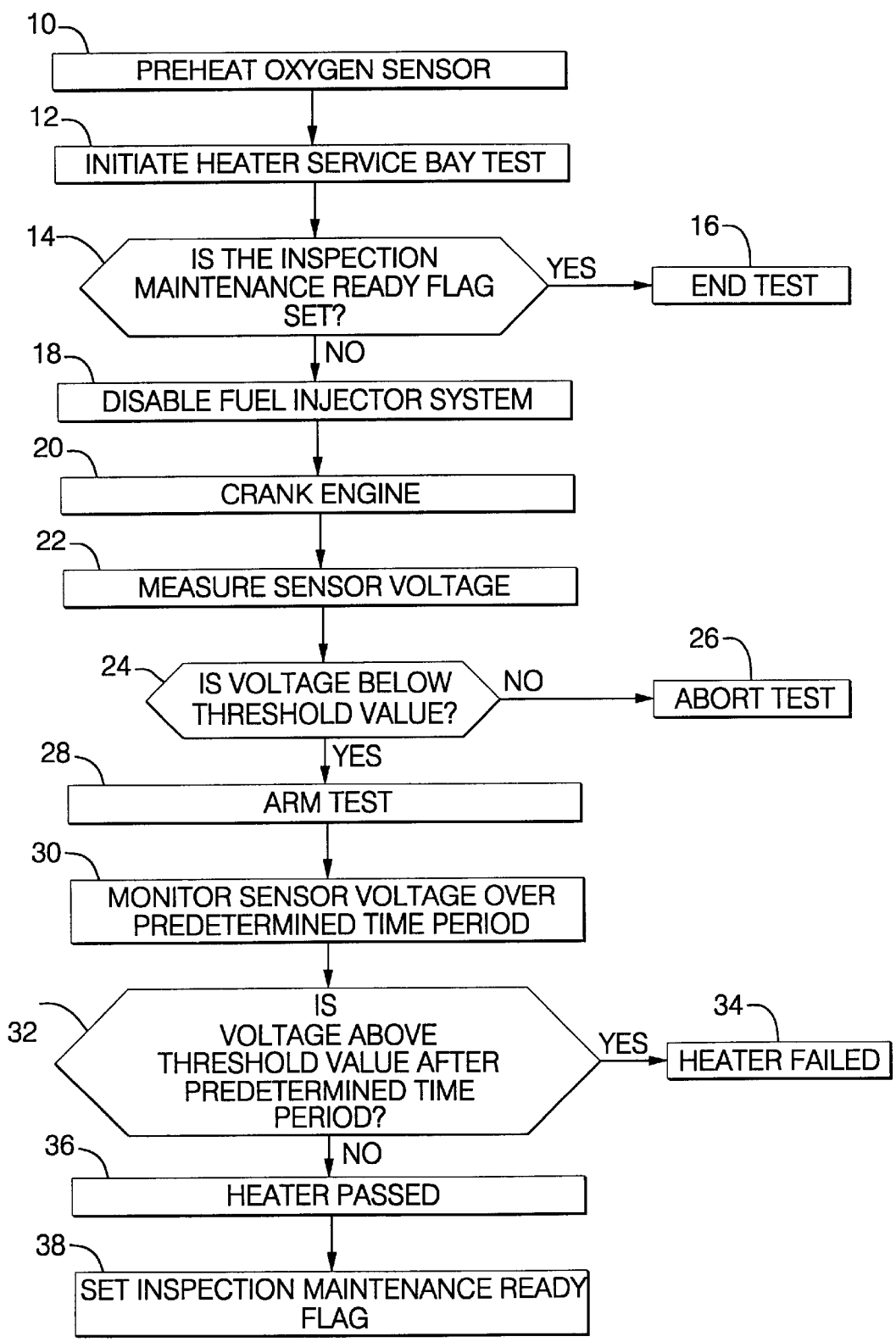
FIG. 1 is a simplified flow diagram of a diagnostic routine for testing an oxygen sensor heater of an internal combustion engine according to the present invention.

A diagnostic routine for testing an oxygen sensor heater of an internal combustion engine according to the present invention is illustrated in FIG. 1. In its simplest form, the diagnostic subroutine of the present invention includes step 10 for preheating the oxygen sensor heater to insure that the oxygen sensor is sufficiently warm. In step 12, the heater service hay test is initiated. A voltage signal is measured from an oxygen sensor associated with the oxygen sensor heater after a predetermined period of time has passed in step 30. In query 32, it is determined if the voltage signal is greater than a threshold value after the predetermined period of time has elapsed.

If the voltage signal is greater than the threshold value in answer to query 32, the diagnostic routine branches to step 34 where a signal is generated indicating that the oxygen sensor heater failed the diagnostic routine. If the voltage signal is not greater than the threshold value in answer to query 32, a signal is generated indicating that the oxygen sensor heater passed the diagnostic routine in step 36. The voltage signal from the oxygen sensor can be monitored continuously over the predetermined period of time in step 30 if desired.

The diagnostic subroutine according to the present invention can also include the step of setting an inspection maintenance flag to a predetermined value in step 38 after the diagnostic routine has been run once for the particular oxygen sensor heater and the heater has passed the diagnostic routine. In addition, the diagnostic routine according to the present invention can include a query 14 to determine if the inspection maintenance flag is set to a predetermined value prior to measuring step 30. If the inspection maintenance flag is not equal to the predetermined value in query 14, the diagnostic routine continues with measuring 30 and query 32. If the inspection maintenance flag is equal to the predetermined value, the diagnostic subroutine aborts measuring step 30 and query 32 by branching to step 16 which ends the test. The test is ended prior to completion under these circumstances, since the inspection maintenance flag is already set equal to a predetermined value indicating that the diagnostic routine has been run previously on this oxygen sensor heater and the oxygen sensor heater has passed the diagnostic routine.

Preferably, in step 18 the fuel injection system of the internal combustion engine is disabled prior to measuring step 30. The internal combustion engine is cranked in step 20 after the fuel injection system is disabled. Steps 18 and 20 insure that the exhaust environment will be in a lean state. A voltage signal from the oxygen sensor is measured in step 22 after the internal combustion engine has been cranked in step 20. Query 24 then determines if the voltage signal is below a threshold value. If the voltage signal is not below a predetermined threshold value in response to query 24, the diagnostic subroutine branches to step 26 where measuring step 30 and determining query 32 are aborted. If the voltage signal is below the predetermined threshold value in response to query 24, the diagnostic routine continues to step 28 where the test is armed, allowing the diagnostic routine to continue with measuring step 30 and determining query 32.

Figure 2:
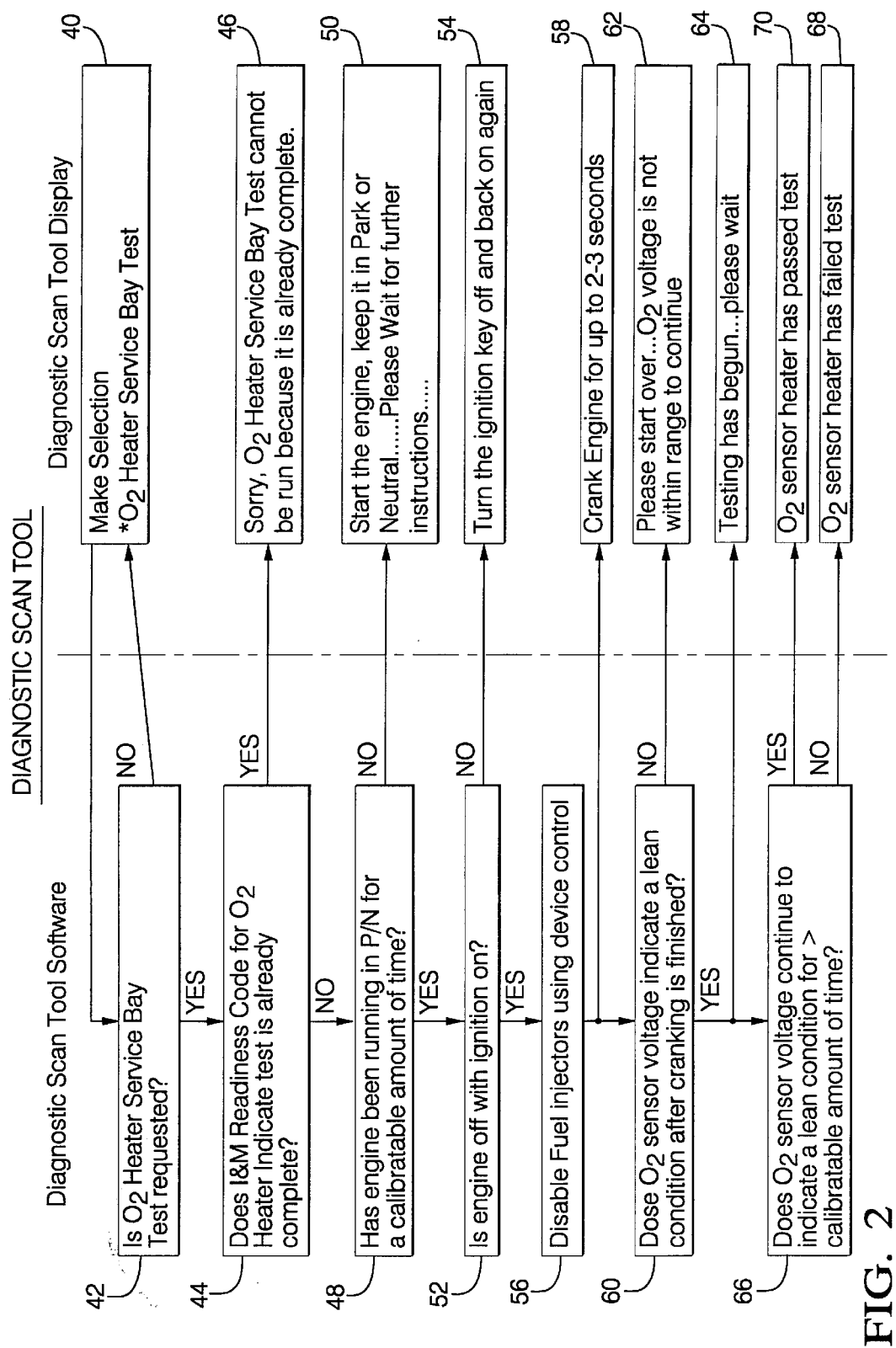
FIG. 2 is a flow diagram of a diagnostic routine according to the present invention with corresponding screen display to the operator of the diagnostic routine.

Referring now to FIG. 2, a simplified schematic flow diagram of the diagnostic scan tool software is shown with reference to associated diagnostic scan tool displays presented to the operator throughout the diagnostic routine to prompt the operator to perform the required procedural steps in the proper order. As can be seen from FIG. 2, the diagnostic scan tool display initially prompts the operator to make a selection in step 40. When the operator has selected the oxygen heater service bay test, the diagnostic scan tool software is initialized.

In query 42 of the diagnostic scan tool software, the diagnostic routine determines if the oxygen heater service bay test has been requested. If the oxygen heater service bay test has not been requested in response to query 42, the program branches back to diagnostic scan tool display step 40 where the operator is prompted to make a selection. If the oxygen heater service bay test has been requested in response to query 42, the diagnostic routine continues to query 44 where the program determines if the inspection maintenance readiness code for the oxygen heater indicates that a test has already been completed.

If the inspection maintenance readiness code indicates that a test has already been completed, the diagnostic routine branches to step 46 where the diagnostic scan tool display prompts the user that the heater service bay test cannot be run because the test is already complete. If the inspection maintenance readiness code indicates that the oxygen heater test has not already been completed in response to query 44, the diagnostic routine continues to query 48 where the program determines if the engine has been running in park or neutral for a predetermined amount of time.

If the engine has not been running in park or neutral for a predetermined period of time in response to query 48, the diagnostic routine branches to step 50 where the diagnostics scan tool display prompts the operator to start the engine, while keeping the transmission in park or neutral and wait for further instructions. If the engine has been running in park or neutral for a predetermined amount of time in response to query 48, the diagnostic routine continues to query 52 where it determine of the engine is off with the ignition turned on.

If the engine is not off or the ignition is not on in response to query 52, the diagnostic routine branches to step 54 where the diagnostic scan tool display prompts the user to turn the ignition key off and then to turn the ignition key back on again. If the engine is off and the ignition is on in response to query 52, the diagnostic routine continues to step 56 where the fuel injectors are disabled using the fuel injector device control.

The diagnostic routine then continues to step 58 where the diagnostic scan tool display prompts the operator to crank the engine for approximately 2 seconds to 3 seconds. The diagnostic routine then continues to query 60 where it is determined if the oxygen sensor voltage indicates a lean condition after cranking of the engine is finished. If the oxygen sensor voltage does not indicate a lean condition after the cranking is finished in response to query 60, the diagnostic routine branches to step 62 where the diagnostic scan tool display prompts the user to start the procedure over since the oxygen sensor voltage is not within an acceptable range to continue. If the oxygen sensor voltage indicates a lean condition after cranking is finished in response to query 60, the diagnostic routine continues to step 64 where the diagnostic tool display prompts the user that the testing has begun and to please wait.

After prompting in step 64, the diagnostic routine continues to query 66 where the program determines if the oxygen sensor voltage continues to indicate a lean condition for more than a predetermined amount of time. If the oxygen sensor voltage does not continue to indicate a lean condition for greater than the predetermined period of time in response to query 66, the diagnostic routine branches to step 68 where the diagnostic scan tool display prompts the user that the oxygen sensor heater has failed the test. If the oxygen sensor voltage continues to indicate a lean condition for greater than the predetermined period of time in response to query 66, the diagnostic routine branches to step 70 where the diagnostic scan tool display prompts the user that the oxygen sensor heater has passed the test.

Figure 3:
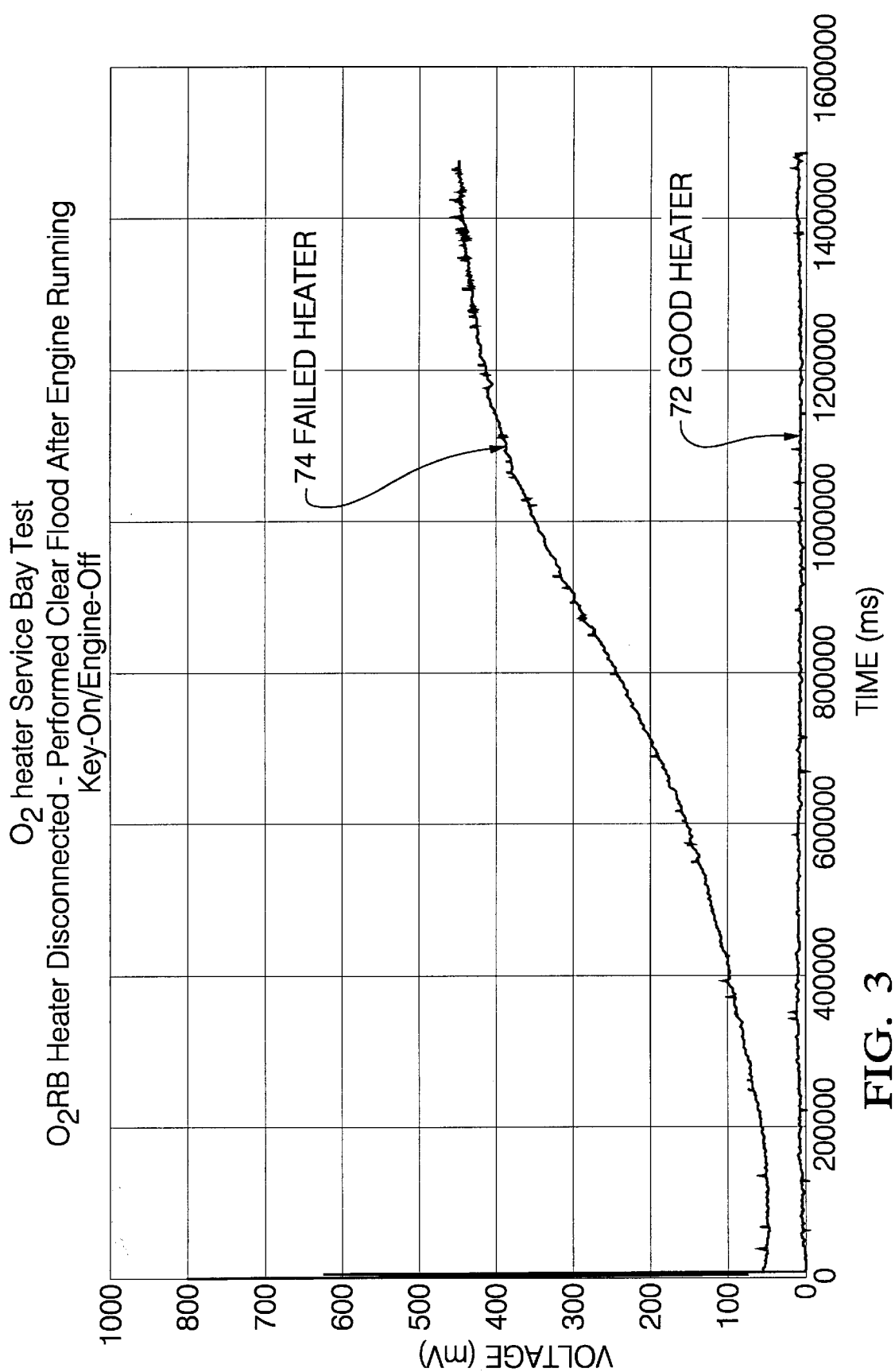
FIG. 3 is a graph illustrating voltage in millivolts versus time in milliseconds, illustrating an example of a failed oxygen sensor heater, and a passed oxygen sensor heater according to the present invention.

Referring now to FIG. 3, a graph of voltage in millivolts versus time in milliseconds illustrates an example of an oxygen sensor heater that has passed the test, labeled as line 72, where the oxygen sensor voltage continues to indicate a lean condition for greater than the predetermined amount of time. By comparison, line 74, by way of example and not limitation, illustrates an oxygen sensor voltage which does not continue to indicate a lean condition for greater than the predetermined period of time by rising in voltage above a predetermined threshold value indicating that the oxygen sensor heater has failed the test.

In operation, the service tool is connected to the vehicle to be tested and provides an operator selected option that allows the test to be initiated. The service bay test will only be run if the vehicle-inspection-maintenance-readiness flag indicates that the onboard oxygen sensor heater diagnostic has never been run before. Once the test is initiated, the service tool prompts the operator to run the vehicle in park or neutral within the service bay for a predetermined period of time to insure that the oxygen sensors present in the vehicle are sufficiently warm. After the oxygen sensors have been sufficiently warmed, the service tool prompts the operator to shut the vehicle engine off and then to return the ignition key to the key-on/engine-off position. The key-on/engine-off position provides power to the oxygen sensors present in the internal combustion engine. With the ignition key in the key-on/engine-off, the service tool according to the present invention disables the fuel injectors and prompts the user to crank the vehicle engine for a predetermined period of time. Cranking the engine for a predetermined period of time insures that the exhaust environment will be in a lean state. The ignition key should remain in the key-on/engine-off position after the cranking interval is complete. The service tool then monitors the oxygen sensor voltage. If the measured voltage is below a predetermined threshold value, then the diagnostic test will be allowed to continue. If the voltage is not below a predetermined threshold value, the operator will be prompted to return to the beginning of the diagnostic test procedure. After the measured voltage has been determined to be below a predetermined threshold value, the service tool monitors the oxygen sensor voltage for a predetermined period of time. If the voltage remains below a predetermined threshold voltage for a predetermined time period, the sensor heater will be considered as passing the diagnostic test. If the measured voltage does not remain below a predetermined threshold voltage for a predetermined time period, the sensor heater will be considered as failing the diagnostic test.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A diagnostic routine for testing a heater for an oxygen sensor of an internal combustion engine comprising the steps of:
   preheating the oxygen sensor heater;
   disabling a fuel injection system of the internal combustion engine;
   cranking the internal combustion engine;
   measuring a voltage signal from the oxygen sensor after a predetermined period of time;
   determining if the voltage signal is greater than a threshold value after the predetermined period of time has elapsed;
   if the voltage signal is greater than the threshold value, signaling the oxygen sensor heater failed the diagnostic routine; and
   if the voltage signal is not greater than the threshold value, signaling the oxygen sensor heater passed the diagnostic routine.

2. The diagnostic routine of claim 1 further comprising the step of:
   monitoring the voltage signal from the oxygen sensor over the predetermined period of time.

3. The diagnostic routine of claim 1 further comprising the step of:
   setting an inspection maintenance flag to a predetermined value after signaling the oxygen sensor heater passed the diagnostic routine.

4. The diagnostic routine of claim 1 further comprising the step of:
   prior to the disabling step, determining if an inspection maintenance flag is set to a predetermined value.

5. The diagnostic routine of claim 4 further comprising the step of:
   if the inspection maintenance flag is not equal to the predetermined value, continuing with the diagnostic routine; and
   if the inspection maintenance flag is equal to the predetermined value, ending the diagnostic routine.

6. A diagnostic routine for testing a heater for an oxygen sensor of an internal combustion engine comprising the steps of:
   preheating the oxygen sensor heater;
   disabling a fuel injection system of the internal combustion engine;
   cranking the internal combustion engine after the fuel injection system is disabled;
   measuring a voltage signal from the oxygen sensor after cranking the internal combustion engine;
   determining if the voltage signal is greater than a threshold value;
   if the voltage signal is greater than the threshold value, aborting the diagnostic routine; and
   if the voltage signal is not greater than the threshold value, continuing with the diagnostic routine.

7. The diagnostic routine of claim 6 further comprising the step of:
   measuring a second voltage signal from the oxygen sensor after a predetermined period of time.

8. The diagnostic routine of claim 7 further comprising the step of:
   if the second voltage signal is not below the threshold value, signaling the oxygen sensor heater failed the diagnostic routine; and
   if the second voltage signal is below the threshold value, signaling the oxygen sensor heater passed the diagnostic routine.

9. A diagnostic routine for testing a heater for an oxygen sensor of an internal combustion engine comprising:
   means for preheating the oxygen sensor heater;
   means for disabling a fuel injection system of the internal combustion engine;
   means for cranking the internal combustion engine;
   means for measuring a voltage signal from the oxygen sensor after a predetermined period of time;
   means for determining if the voltage signal is greater than a threshold value after the predetermined period of time has elapsed;
   means for signaling the oxygen sensor heater failed the diagnostic routine if the voltage signal is greater than the threshold value; and
   means for signaling the oxygen sensor heater passed the diagnostic routine if the voltage signal is not greater than the threshold value.

10. The diagnostic routine of claim 9 further comprising:
    means for monitoring the voltage signal from the oxygen sensor over the predetermined period of time.

11. The diagnostic routine of claim 9 further comprising:
    means for setting an inspection maintenance flag to a predetermined value after the signaling means signals the oxygen sensor heater passed the diagnostic routine.

12. The diagnostic routine of claim 9 further comprising:
    means for determining if an inspection maintenance flag is set to a predetermined value prior to the disabling means disabling the fuel injection system of the internal combustion engine.

13. The diagnostic routine of claim 12 further comprising:
    means for continuing the diagnostic routine if the inspection maintenance flag is not equal to the predetermined value; and
    means for ending the diagnostic routine if the inspection maintenance flag is equal to the predetermined value.

14. A diagnostic routine for testing a heater for an oxygen sensor of an internal combustion engine comprising:
    means for preheating the oxygen sensor heater;
    means for disabling a fuel injection system of the internal combustion engine;
    means for cranking the internal combustion engine;
    means for measuring a voltage signal from the oxygen sensor after cranking the internal combustion engine;
    means for determining if the voltage signal is greater than a threshold value;
    means for aborting the diagnostic routine if the voltage signal is greater than the threshold value; and
    means for continuing with the diagnostic routine if the voltage signal is not greater than the threshold value.

15. The diagnostic routine of claim 14 further comprising:
    means for measuring a second voltage signal from the oxygen sensor after a predetermined period of time.

16. The diagnostic routine of claim 15 further comprising:
    means for signaling the oxygen sensor heater failed the diagnostic routine, if the second voltage signal is not below the threshold value; and
    means for signaling the oxygen sensor heater passed the diagnostic routine, if the second voltage signal is below the threshold value.

* * * * *